United States Patent [19]
Hamanaka

[11] Patent Number: 5,565,472
[45] Date of Patent: Oct. 15, 1996

[54] 4-ARYL-3-(HETEROARYLUREIDO)-1,2-DIHYDRO-2-OXO-QUINOLINE DERIVATIVES AS ANTIHYPERCHOLESTEROLEMIC AND ANTIATHEROSCLEROTIC AGENTS

[75] Inventor: Ernest S. Hamanaka, Gales Ferry, Conn.

[73] Assignee: Pfizer Inc., New York, N.Y.

[21] Appl. No.: 256,303

[22] PCT Filed: Dec. 21, 1992

[86] PCT No.: PCT/US92/10886

§ 371 Date: Oct. 18, 1994

§ 102(e) Date: Oct. 18, 1994

[51] Int. Cl.⁶ .................. A61K 31/47; C07D 215/22
[52] U.S. Cl. .................. 514/312; 514/243; 514/248; 514/256; 514/258; 544/183; 544/235; 544/322; 544/328; 546/156; 546/157
[58] Field of Search ................. 514/243, 248, 514/258, 256, 312; 544/183, 235, 322, 328; 546/156, 157

[56] References Cited

U.S. PATENT DOCUMENTS

| | | | |
|---|---|---|---|
| 4,623,662 | 11/1986 | De Vries | 514/596 |
| 4,716,175 | 12/1987 | Hoefle et al. | 514/357 |
| 4,743,605 | 5/1988 | Hoefle et al. | 514/269 |

FOREIGN PATENT DOCUMENTS

| | | |
|---|---|---|
| 0354994 | 2/1990 | European Pat. Off. . |
| 0421456 | 4/1991 | European Pat. Off. . |
| 9104027 | 4/1991 | WIPO . |
| 9112249 | 8/1991 | WIPO . |
| 9219614 | 11/1992 | WIPO . |

*Primary Examiner*—Yogendra N. Gupta
*Attorney, Agent, or Firm*—Peter C. Richardson; Paul H. Ginsburg; Seymour G. Bekelnitzky

[57] ABSTRACT

Compounds of the formula

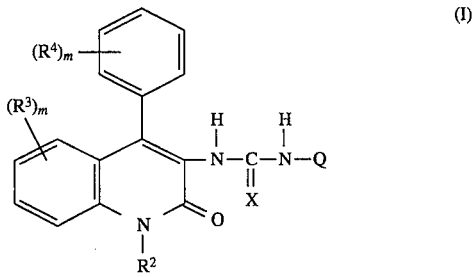

the pharmaceutically acceptable salts thereof wherein $R^2$, $R^3$, $R^4$, m, X and Q are as defined below, and novel intermediates used in the synthesis of such compounds. The compounds of formula I are inhibitors of acyl coenzyme A: cholesterol acyltransferase (ACAT) and are useful as hypolipidemic and antiatherosclerosis agents.

11 Claims, No Drawings

4-ARYL-3-(HETEROARYLUREIDO)-1,2-DIHYDRO-2-OXO-QUINOLINE DERIVATIVES AS ANTIHYPERCHOLESTEROLEMIC AND ANTIATHEROSCLEROTIC AGENTS

BACKGROUND OF THE INVENTION

The present invention relates to new 4-aryl-3-(heteroarylureido)- 1,2-dihydro-2-oxo-quinoline derivatives, pharmaceutical compositions comprising such compounds, novel 3-(p-nitrobenzyloxycarbonylamino) quinoline intermediates used in the synthesis of such compounds and the use of such compounds to inhibit intestinal absorption of cholesterol, lower serum cholesterol and reverse the development of atherosclerosis. The compounds are inhibitors of acyl coenzyme A: cholesterol acyltransferase (ACAT).

Cholesterol that is consumed in the diet (dietary cholesterol) is absorbed as free cholesterol by the mucosal cells of the small intestine. It is then esterified by the enzyme ACAT, packaged into particles known as chylomicrons, and released into the bloodstream. Chylomicrons are particles into which dietary cholesterol is packaged and transported in the bloodstream. By inhibiting the action of ACAT, the compounds of this invention prevent intestinal absorption of dietary cholesterol and thus lower serum cholesterol levels. They are therefore useful in preventing atherosclerosis, heart attacks and strokes.

By inhibiting the action of ACAT, the compounds of the present invention also enable cholesterol to be removed from the walls of blood vessels. This activity renders such compounds useful in slowing or reversing the development of atherosclerosis as well as in preventing heart attacks and strokes.

Other inhibitors of ACAT are referred to in U.S. Pat. Nos. 4,716,175 and 4,743,605 (a divisional of the '175 patent), the European Patent Applications having publication numbers 0 242 610, 0 245 687, 0 252 524, and 0 354 994, and U.S. patent application Ser. No. 07/648,677, filed Jan. 31, 1991 and assigned in common with the present application.

Certain ureas and thioureas as antiatherosclerosis agents are referred to in U.S. Pat. No. 4,623,662 and in the European Patent Applications having publication numbers 0 335 374, 0 386 487, 0 370 740, 0 405 233 and 0 421 456.

SUMMARY OF THE INVENTION

The present invention relates to compounds of the formula

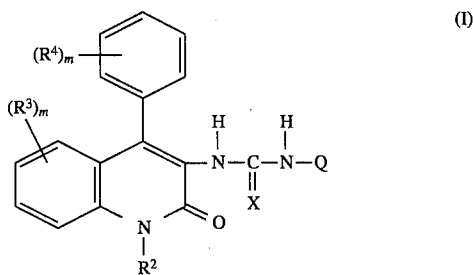

wherein each m is independently selected from 0 to 4;
$R^2$ is selected from hydrogen and $(C_1-C_6)$ alkyl; Each $R^3$ and $R^4$ is independently selected from halogen, $(C_1-C_6)$ alkyl optionally substituted with one or more halogen atoms, $(C_1-C_6)$ alkoxy optionally substituted with one or more halogen atoms, $(C_1-C_6)$ alkylthio optionally substituted with one or more halogen atoms; nitro, carboxyl optionally esterified with a $(C_1-C_6)$ alkyl group; hydroxyl, $(C_1-C_4)$ acyloxy and $(C_1-C_3)$ acyl;
X is sulfur or oxygen; and
Q is a group of the formula

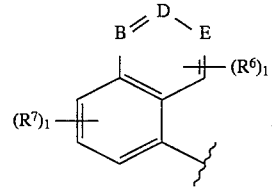

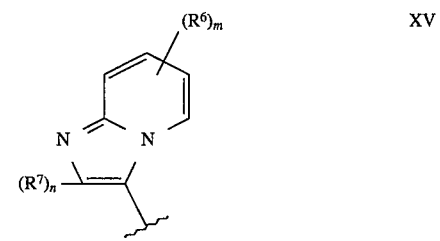

OR

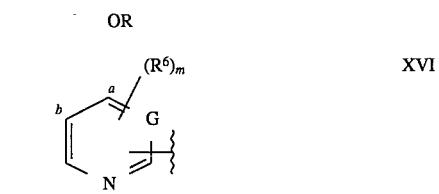

wherein m is as defined above;
n is 0 or 1.
Each l is independently selected from 0 to 3;
Each $R^6$ and $R^7$ is independently selected from the group consisting of halogen, $(C_1-C_6)$alkyl, $(C_1-C_6)$ haloalkyl, optionally halogenated $(C_1-C_6)$alkoxy, $(C_1-C_6)$ alkylthio, $(C_5-C_7)$ cycloalkylthio, optionally substituted phenyl-$(C_1-C_6)$alkylthio, substituted phenylthio, heteroarylthio, heteroaryloxy, $(C_1-C_6)$ alkylsulfinyl, $(C_1-C_6)$ alkylsulfonyl, $(C_5-C_7)$ cycloalkylsulfinyl, $(C_5-C_7)$ cycloalkylsulfonyl, phenyl $(C_1-C_6)$ alkylsulfinyl, phenyl $(C_1-C_6)$ alkylsulfonyl, substituted phenylsulfinyl, substituted phenylsulfonyl, heteroarylsulfinyl, heteroarylsulfonyl, and $NR^{10}R^{11}$, wherein $R^{10}$ and $R^{11}$ are the same or different and are selected from the group consisting of hydrogen, $(C_1-C_6)$ alkyl, optionally substituted phenyl, $(C_1-C_6)$ acyl and optionally substituted aroyl, wherein said substituted phenyl and substituted aroyl groups are substituted with one or more substituents independently selected from the group consisting of $(C_1-C_6)$ alkyl, $(C_1-C_6)$ alkoxy, $(C_1-C_6)$ alkylthio, halogen and trifluoromethyl, or $R^{10}$ and $R^{11}$, together with the nitrogen to which they are attached, form a piperidine, pyrrolidine or morpholine ring;

B, D, E and G are selected from the group consisting of nitrogen and carbon, with the proviso that one or more of B, D and E is nitrogen, and with the proviso that when G is nitrogen, the group XVI is attached to the nitrogen of formula I at the 4 or 5 position of the pyrimidine ring (designated by a and b) wherein any of said nitrogens may be oxidized;

or a pharmaceutically acceptable salt of such compound.

Unless otherwise indicated, the term "halogen" as used herein, includes fluoro, chloro, bromo and iodo.

Unless otherwise indicated, the term "alkyl" as used herein, may be straight, branched or cyclic, and may include straight and cyclic moieties as well as branched and cyclic moieties.

Unless otherwise indicated, the term "one or more substituents" or "one or more halogen atoms" as used herein, refers to from one to the maximum number of substituents possible based on the number of available bonding sites.

The present invention also relates to compounds of the formula

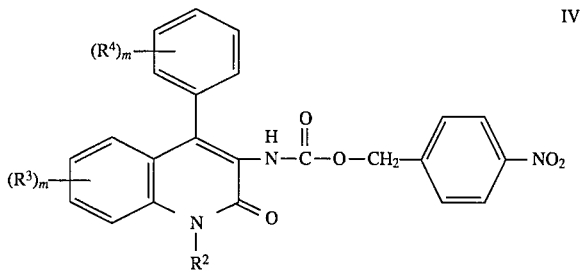

wherein m, $R^2$, $R^3$ and $R^4$ are as defined above. These compounds are useful as intermediates in the synthesis of compounds of the formula I.

Preferred compounds of formula I are those wherein Q is 6- ($C_1$–$C_3$)alkoxyquinolin-5-yl, 6-($C_1$–$C_3$) alkylthioquinolin-5-yl, 6-($C_1$–$C_3$)alkylquinolin-5-yl, 6-($C_1$–$C_3$)alkylthioisoquinolin-5-yl, 6-($C_1$–$C_3$)alkoxyisoquinolin-5-yl, 4,6-bis[($C_1$–$C_3$)alkylthio]-2-methylpyrimidin-5-yl, 4,6-bis[($C_1$–$C_3$)alkylthio]pyrimidin-5-yl, 2,4-bis[($C_1$–$C_3$)alkylthio]-6-methylpyridin-3-yl or 2,4-bis[($C_1$–$C_3$)alkylthio]pyridin-3-yl.

Other preferred compounds of the formula I are those wherein $R^2$ is methyl, m is at least one and $R^3$ and $R^4$ defined as above with the proviso that at least one of $R^3$ is 6-halo or 6-alkyl and at least one of $R^4$ is 2-halo.

More preferred compounds of the formula I are those wherein Q is 6-methoxyquinolin-5-yl, 6-methylthioquinolin-5-yl, 6-methoxyisoquinolin-5-yl, 6-methylthioisoquinolin-5-yl, 2-methyl-4,6-bis(methylthio)pyrimidin-5-yl, 6-methyl-2,4-bis(methylthio)pyridin-3-yl, 2,4-bis(ethylthio)pyridin-3-yl, and 2,4-dimethoxy-6-methylpyridin-3-yl.

Other compounds of formula I include those wherein Q is 2,4,6-trimethylpyridin-3-yl, and 6-(4-methoxyphenylthio)quinolin-5-yl.

Specific preferred compounds of formula I include:
N-[2,4-Bis(methylthio)-6-methylpyridin-3-yl]-N'-[6-chloro- 4-(2-chlorophenyl)-1,2-dihydro-1-methyl-2-oxoquinolin- 3-yl]urea;

N-[4,6-Bis(methylthio)2-methylpyrimidin-5-yl]-N'-[6-chloro- 4-(2-chlorophenyl)-1,2-dihydro-1-methyl-2-oxoquinolin- 3-yl]urea;

N-[6-Chloro-4-(2-chlorophenyl)-1,2-dihydro-1-methyl-2-oxoquinolin- 3-yl]-N'-(6-methylthioquinolin-5-yl)urea;

N-[6-Chloro-4-(2-chlorophenyl)-1,2-dihydro-1-methyl-2-oxoquinolin- 3-yl]-N'-(6-methoxyquinolin-5-yl)urea;

N-[4,6-Bis(methylthio)-2-methylpyrimidin-5-yl]-N'-[4-(2-chlorophenyl)-1,2-dihydro-6-ethyl-1-methyl-2-oxoquinolin- 3-yl]urea;

N-[2,4-Bis(methylthio)-6-methylpyridin-3-yl]-N'-[4-(2-chlorophenyl)- 1,2-dihydro-6-ethyl-1-methyl-2-oxoquinolin-3-yl]urea;

N-4-(2-Chlorophenyl)-1,2-dihydro-6-ethyl-1-methyl-2-oxoquinolin- 3-yl]-N'-(6-methylthioquinolin-5-yl)urea;

N-[4-(2-Chlorophenyl)-1,2-dihydro-6-ethyl-1-methyl-2-oxoquinolin- 3-yl]-N'-(6-methoxyquinolin-5-yl)urea;

N-[2,4-Bis(methylthio)-6-methylpyridin-3-yl]-N'-[4-(2-chlorophenyl)- 1,2-dihydro-6-isopropyl-1-methyl-2-oxoquinolin- 3-yl]urea;

N-[4,6-Bis(methylthio)-2-methylpyrimidin-5-yl]-N'-[4-(2-chlorophenyl)-1,2-dihydro-6-isopropyl-1-methyl-2-oxoquinolin- 3-yl]urea;

N-[4-(2-Chlorophenyl)-1,2-dihydro-6-isopropyl-1-methyl- 2-oxoquinolin-3-yl]-N'-(6-methylthioquinolin-5-yl)urea;

N-[4-(2-Chlorophenyl)-1,2-dihydro-6-isopropyl-1-methyl- 2-oxoquinolin-3-yl]-N'-(6-methoxyquinolin-5-yl)urea;

N-[2,4-Bis(methylthio)-6-methylpyridin-3-yl]-N'-[4-(2-chlorophenyl)- 1,2-dihydro-1,6-dimethyl-2-oxoquinolin-3yl]urea;

N-[4-(2-Chlorophenyl)-1,2-dihydro-1,6-dimethyl-2-oxoquinolin- 3-yl]-N'-(6-methylthioquinolin-5-yl)urea;

N-[4,6-Bis (methylthio)-2-methylpyrimidin-5-yl]-N'-[4-(2-chlorophenyl)-1,2-dihydro-1,6-dimethyl-2-oxoquinolin-3-yl]urea;

N-[4-(2-Chlorophenyl)-1,2-dihydro-1,6-dimethyl-2-oxoquinolin- 3-yl]-N'-(6-methoxyquinolin-5-yl)urea;

N-[6-Chloro-4-(2-chlorophenyl)-1,2-dihydro-1-methyl-2-oxoquinolin- 3-yl]-N'-(6-dimethylaminoquinolin-5-yl)urea;

N-[6-Chloro-4-(2-chlorophenyl)-1,2-dihydro-1-methyl-2-oxoquinolin- 3-yl]-N'-(2-dimethylamino-6-methyl-4-methylthiopyridin- 3-yl)urea;

N-[6-Chloro-4-(2-chlorophenyl)-1,2-dihydro-1-methyl-2-oxoquinolin- 3-yl]-N'-(6-methoxyisoquinolin-5-yl)urea.

The present invention also relates to all radiolabelled forms of the compounds of the formulae I and II, including those comprising tritium and/or carbon-14 ($^{14}C$). Such radiolabelled compounds are useful as research and diagnostic tools in metabolism pharmacokinetic studies and in binding assays in both animals and man.

The present invention also relates to a pharmaceutical composition for inhibiting ACAT, inhibiting intestinal absorption of cholesterol, reversing or slowing the development of atherosclerosis, or lowering the concentration of serum cholesterol in a mammal, including a human, comprising an amount of a compound of the formula I, or a pharmaceutically acceptable salt thereof, effective in inhibiting ACAT, inhibiting intestinal absorption of cholesterol, reversing or slowing the development of atherosclerosis, or lowering the concentration of serum cholesterol, and a pharmaceutically acceptable carrier.

The present invention also relates to a method for inhibiting ACAT, inhibiting intestinal absorption of cholesterol, reversing or slowing the development of atherosclerosis, or lowering the concentration of serum cholesterol in a mammal, including a human, comprising administering to a mammal an amount of a compound of the formula I, or a pharmaceutically acceptable salt thereof, effective in inhibiting ACAT, inhibiting intestinal absorption of cholesterol, reversing or slowing the development of atherosclerosis, or lowering the concentration of serum cholesterol.

Examples of pharmaceutically acceptable acid addition salts of the compounds of formula I salts are the salts of hydrochloric acid, p-toluenesulfonic acid, fumaric acid, citric acid, succinic acid, salicyclic acid, oxalic acid, hydrobromic acid, phosphoric acid, methanesulfonic acid, tartaric acid, di-p-toluoyl tartaric acid, and mandelic acid.

DETAILED DESCRIPTION OF THE INVENTION

Reaction scheme 1 below illustrates the synthesis of the compounds of this invention. Except where otherwise stated, $R^1$, $R^2$, $R^3$, $R^4$, $R^6$, $R^7$, $R^{10}$, $R^{11}$, $R^{12}$, $R^{13}$, Q, X, B, D, E, and G, l, m and n in the reaction scheme and discussion that follows are defined as above.

Scheme 1

Scheme 1 illustrates the preparation of compounds of formula I wherein $R^1$ is hydrogen. The starting materials II and III may be prepared by known methods (see, e.g., Ikeda, et al., European Patent Application 0 421.456 A2).

The compounds of formula III are then converted to the novel compounds of formula IV by reaction with p-nitrobenzyl alcohol in the presence of dibutyltin oxide.

Reaction of the amino compounds of formula V with isocyanato group forming compounds, such as trichloromethyl chloroformate regenerates the compounds of formula II in a more highly purified state than when produced from the compounds of formula II.

SCHEME 1

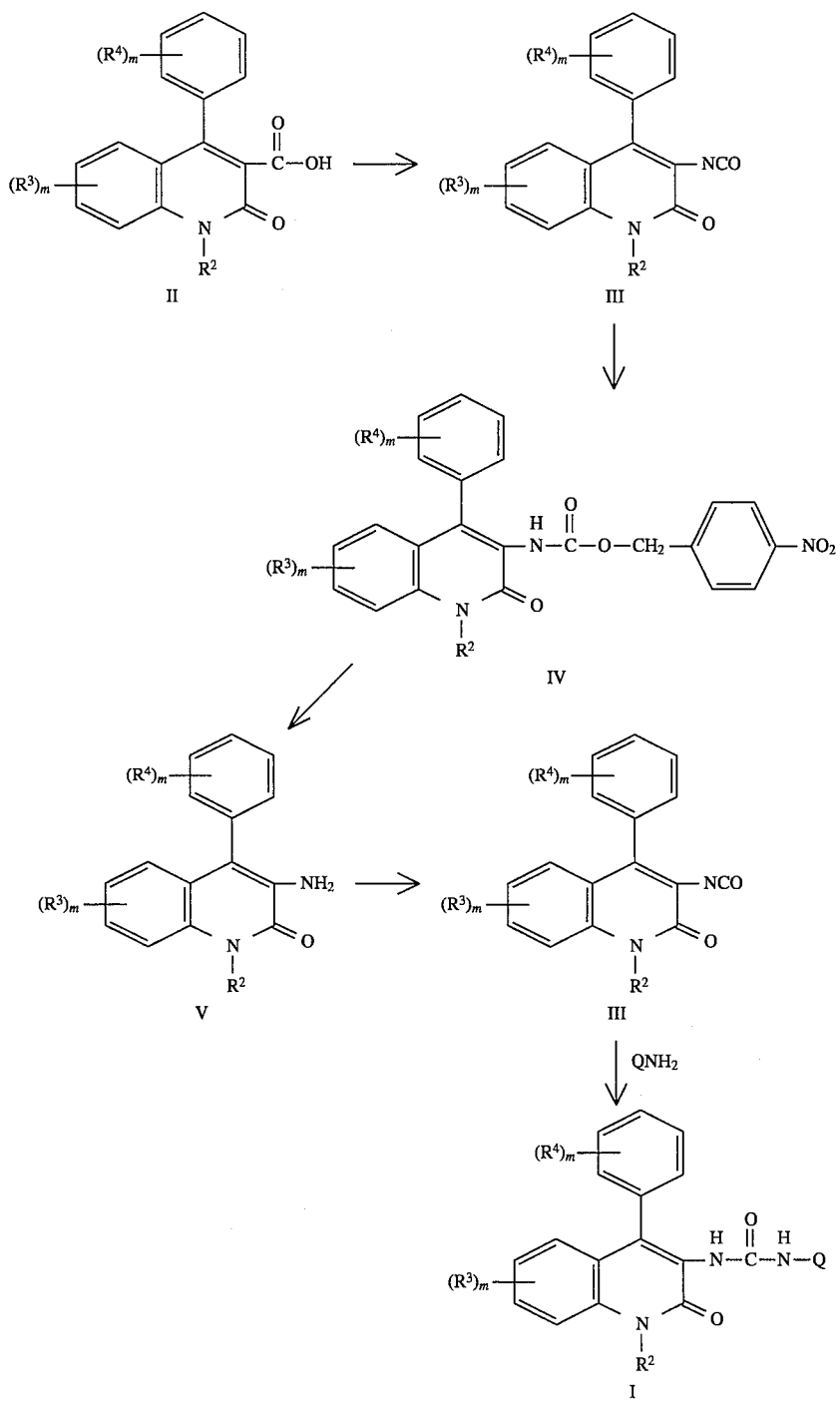

The compounds of formula IV are reduced by hydrogen, in the presence of Raney nickel, to form the amines of formula V.

The compound of formula III, prepared as above, is then reacted with a compound of the formula QNH$_2$, wherein Q is defined as above, to form the compound of formula I.

The preparation of compounds of the formula QNH$_2$ is described in my co-pending application Ser. No. 07/692,323.

In an alternative method the compound of formula I may be prepared by reacting a compound of the formula V with a compound of the formula QNC=X, whose preparation is disclosed in said application, wherein Q and X are as defined as above.

The novel compounds of formula I and the pharmaceutically acceptable salts thereof are useful as inhibitors of acyl coenzyme A: cholesterol acyltransferase (ACAT). As such they inhibit intestinal absorption of cholesterol in mammals and are useful in the treatment of high serum cholesterol in mammals, including humans. As used herein, treatment is meant to include both the prevention and alleviation of high serum cholesterol. The compound may be administered to a subject in need of treatment by a variety of conventional routes of administration, including orally, parenterally and topically. In general, these compounds will be administered orally or parenterally at dosages between about 0.5 and about 30 mg/kg body weight of the subject to be treated per day, preferably from about 0.8.to 5 mg/kg. For an adult human of approximately 70 kg of body weight, the usual dosage would, therefore, be about 3.5 to about 2000 mg per day. However, some variation in dosage will necessarily occur depending on the condition of the subject being treated and the activity of the compound being employed. The person responsible for administration will, in any event, determine the appropriate dose for the individual subject.

A compound of formula I or a pharmaceutically acceptable salt thereof may be administered alone or in combination with pharmaceutically acceptable carriers, in either single or multiple doses. Suitable pharmaceutical carriers include inert solid diluents or fillers, sterile aqueous solution and various organic solvents. The resulting pharmaceutical compositions are then readily administered in a variety of dosage forms such as tablets, powders, lozenges, syrups, injectable solutions and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions of a compound of formula I or a pharmaceutically acceptable salt thereof in sesame or peanut oil, aqueous propylene glycol, or in sterile aqueous solution may be employed. Such aqueous solutions should be suitably buffered if necessary and the liquid diluent first rendered isotonic with sufficient saline or glucose. Such solutions are especially suitable for intravenous, intramuscular, subcutaneous and intraperitioneal administration. In this connection, the sterile aqueous media employed are all readily available by standard techniques known to those skilled in the art.

The activity of the compounds of the present invention as ACAT inhibitors may be determined by a number of standard biological or pharmacological tests. For example, the following procedure was used to determine the ACAT inhibiting activity of compounds of formula I. ACAT was assayed in microsomes isolated from chow fed Sprague-Dawley rats according to Bilheimer, J. T., Meth. Enzymol., 111, ps 286–293 (1985), with minor modifications. Microsomes from rat liver were prepared by differential centrifugation and washed with assay buffer prior to use. The assay mixture contained 25 ul of BSA (40 mg/ml), 30 ul of rat liver microsome solution (100 ug microsomal protein), 20 ul of assay buffer (0.1 M K$_2$PO$_4$, 1.0 mM reduced Glutathione, pH 7.4), 20 ug of cholesterol in 100 ul of a 0.6% Triton WR-1339 solution in assay buffer, and 5 ul of test compound dissolved in 100% DMSO (total volume=180 ul). The assay mixture was incubated for 30 min at 37° C. The reaction was started by the addition of 20 ul of 14° C.-Oleoyl-CoA (1000 uM, 2,000 dpm/nmol) and run for 15 min at 37° C. The reaction was stopped by the addition of 1 ml ETOH. The lipids were extracted into 4 ml hexane. A 3 ml aliquot was dried under N$_2$, and resuspended in 100 ul of chloroform. 50 ul of chloroform were spotted on a heat activated TLC plate and developed in hexane: diethyl ether: acetic acid (85:15:1, v:v:v). Incorporation of radioactivity into cholesteryl esters was quantified on a Berthold LB2842 Linear TLC Analyzer. ACAT inhibition was calculated relative to a DMSO control assay.

The activity of the compounds of formula I in inhibiting intestinal absorption of cholesterol may be determined by the procedure of Melchoir and Harwell, *J. Lipid. Res.*, 26, 306–315 (1985).

The present invention is illustrated by the following examples. It will be understood, however, that the invention is not limited to the specific details of these examples. Melting points are uncorrected. Proton nuclear magnetic resonance spectra ($^1$H NMR) and C$^{13}$ nuclear magnetic resonance spectra (C$^{13}$ NMR) were measured for solutions in deuterochoroform (CDCl$_3$) or D$_6$-dimethylsulfoxide (DMSO-D$_6$)and peak positions are expressed in parts per million (ppm) downfield from tetramethylsilane (TMS). The peak shapes are denoted as follows: s, singlet; d, doublet; t, triplet; q, quartet; m, multiplet; b, broad; c, complex; h, heptet.

EXAMPLE 1

6-Chloro-4-(2-chlorophenyl)-1,2-dihydro-1-methyl-3-(4-nitrobenzyl)oxycarbonylamino)-2-oxoquinoline Triethylamine (0.7 ml, 5 mmol) was added dropwise with stirring at room temperature to a solution of 6-chloro-4-(2-chlorophenyl)- 1,2-dihydro-1-methyl-2-oxoquinoline-3-carboxylic acid (1.75 g, 5 mmol) and diphenylphosphoryl azide (1.19 ml, 5.5 mmol) in 35 ml benzene. The mixture was stirred at room temperature for 15 minutes and then refluxed for 30 minutes to yield a solution of 6-chloro-4-(2-chlorophenyl)- 1,2-dihydro-3-isocyanato-1-methyl-2-oxoquinoline. 4-Nitrobenzyl alcohol (2.31 g, 15.1mmol) and dibutyltin oxide (35 mg) were added to the cooled reaction mixture which was then refluxed for 4 h. The reaction solution was cooled to room temperature, washed with water, dried (sodium sulfate) and concentrated in vacuo. The solid residue was purified by column chromatography on silica gel (650 g), eluting with 3:2 hexane/ethyl acetate to yield the title compound as an off-white solid (1.9 g, 76% yield).

¹H NMR (300 MHz, CDCl₃) δ3.70 (s, 3H), 5.07 (s, 2H), 6.83 (s, 1H), 7.10 (d, 1H), 7.24–7.46 (c, 6H), 7.53 (c, 2H), 8.14 (d, 2H).

In a similar manner, the following 1-methyl-3-(4-nitrobenzyloxycarbonylamino)- 2-oxoquinoline derivatives were prepared:

EXAMPLE 2

4-(2-Chlorophenyl)-1,2-dihydro-6-ethyl-1-methyl-3-(4-nitrobenzyloxycarbonylamino)-2-oxoquinolin 91% yield ¹H NMR (300 MHz, CDCl₃) δ1.15 (t, 3H), 2.59 (q, 2H), 3.84 (s, 3H), 5.08 (s, 2H), 6.72 (s, 1H), 6.92 (s, 1H), 7.22–7.47 (c, 7H), 7.53 (d, 1H), 8.14 (d, 2H).

EXAMPLE 3

4-(2-Chlorophenyl)-1,2-dihydro-6-isopropyl-1-methyl-3-(4-nitrobenzyloxycarbonylamino)-2-oxoquinoline 96% yield.

H NMR (300 MHz, CDCl₃) δ1.16 (d, 3H), 1.17 (d, 3H), 2.85 (h, 1H), 3.84 (s, 3H), 5.08 (s, 2H), 6.74 (s, 1H), 6.96 (d, 1H), 7.25–7.56 (c, 8H), 8.14 (d, 2H).

EXAMPLE 4

4-(2-Chlorophenyl)-1,2-dihydro-1,6-dimethyl-3-(4-nitrobenzyloxycarbonylamino)-2-oxoquinoline 74% yield.

¹H NMR (300 MHz, CDCl₃) δ2.30 (s, 3H), 3.84 (s, 3H), 5.08 (s, 2H), 6.70 (s, 1H), 6.90 (s, 1H), 7.27–7.44 (c, 7H), 7.54 (d, 1H), 8.14 (d, 2H).

EXAMPLE 5

3-Amino-6-chloro-4-(2-chlorophenyl)-1,2-dihydro-1-methyl-2-oxoquinoline

A mixture of 6-chloro-4-(2-chlorophenyl)-1,2-dihydro-1-methyl- 3-(4-nitrobenzyloxycarbonylamino)-2-oxoquinoline (1.9 g, 3.8 mmol) and Raney nickel (1.9 g, 50% slurry in water) in 75 ml dioxane and 75 ml methanol was shaken under hydrogen (50 psi) in a Parr hydrogenation apparatus for 3 h. The catalyst was filtered and the filtrate was concentrated to dryness in vacuo. The residue was dissolved in 100 ml ethyl acetate and the solution was washed with 60 ml brine. The ethyl acetate solution was then dried (sodium sulfate) and concentrated in vacuo to a solid (1.2 g) which was purified by column chromatography on silica gel (150 g), eluting with 7:3 hexane/ethyl acetate to yield the title compound as an off-white solid (950 mg, 79% yield).

¹ H NMR (300 MHz, CDCl₃) δ3.85 (s, 3H), 4.39 (b, 2H), 6.83 (d, 1H), 7.28 (c, 3H), 7.46 (c, 2H), 7.62 (c, 1H).

In a similar manner, the following 3-amino-1,2-dihydro-1-methyl-2-oxoquinoline derivatives were prepared:

EXAMPLE 6

3-Amino-4-(2-chlorophenyl)-1,2-dihydro-6-ethyl-1-methyl-2-oxoquinoline

80% yield.

¹H NMR (300 MHz, CDCl₃) δ1.15 (t, 3H), 2.57 (q, 2H), 3.86 (s, 3H), 4.27 (b, 2H), 6.68 (s, 1H), 7.15–7.35 (c, 3H), 7.45 (m, 2H), 7.63 (m, 1H).

EXAMPLE 7

3-Amino-4-(2-chlorophenyl)-1,2-dihydro-6-isopropyl-1-methyl-2-oxoquinoline

89% yield.

¹H NMR (300 MHz, CDCl₃) δ1.16 (d, 3H), 1.163 (d, 3H), 2.82 (h, 1H), 3.86 (s, 3H), 4.27 (b, 2H), 6.70 (d, 1H), 7.24 (m, 1H), 7.33 (m, 2H), 7.46 (m, 2H), 7.62 (m, 1H).

EXAMPLE 8

3-Amino-4-(2-chlorophenyl)-1,2-dihydro-1,6-dimethyl-2-oxoquinoline

97% yield.

¹H NMR (300 MHz, CDCl₃) δ2.28 (s, 3H), 3.85 (s, 3H), 4.27 (b, 2H), 6.66 (s, 1H), 7.16 (q, 1H), 7.3 (m, 2H), 7.46 (m, 7.63 (m, 1H).

EXAMPLE 9

N-[2,4-Bis(methylthio)-6-methylpyridin-3-yl]-N'-[6-chloro-4-(2-chlorophenyl)-1,2-dihydro-1-methyl-2-oxoquinolin-3-yl]urea A solution of a 3-amino-6-chloro-4-(2-chlorophenyl)-1,2-dihydro-1-methyl-2-oxoquinoline (200 mg, 0.63 mmol) and trichloromethyl chloroformate (0.053 ml, 0.31 mmol) in 5 ml dichloromethane was refluxed under nitrogen overnight. The reaction solution was cooled and concentrated in vacuo to a solid, 6-chloro-4-(2-chlorophenyl)-1,2-dihydro-3-isocyanato- 1-methyl-2-oxoquinoline (214 mg, 99% yield). The isocyanate (107 mg, 0.31 mmol) was dissolved in dimethylformamide (1 ml), 3-amino-2,4-bis(methylthio)-6-methylpyridine (62 mg, 0.31 mmol) was added and the resulting solution was heated overnight under nitrogen at 80° C. The reaction mixture was cooled to room temperature, diluted with 50 ml ethyl acetate and the resulting solution was washed with 3×25 ml water and 25 ml brine, dried (sodium sulfate) and concentrated vacuo. The solid residue (130 mg) was purified by column chromatography on silica gel (75 g), eluting with 3:1 dichloromethane/ethyl acetate to yield the title compound as a white solid (70 mg, 41% yield).

¹H NMR (300 MHz, CDCl₃) δ 2.33 (s, 3H), 2.43 (s, 3H), 2.46 (s, 3H), 3.79 (s, 3H), 6.58 (s, 1H), 6.88 (b, 1H), 7.07 (d, 1H), 7.28–7.54 (c, 7H).

In a similar, the following (1,2-dihydro-1-methyl-2-oxoquinolin- 3-yl)urea derivatives were prepared:

EXAMPLE 10

N-[4,6-Bis(methylthio)2-methylpyrimidin-5-yl]-N'-[6-choloro-4-(2-chlorophenyl)-1,2-dihydro-1-methyl-2-oxoquinolin-3-yl]urea 13% yield.

$^1$H NMR (300 MHz, CDCl$_3$) δ2.43 (s, 6H), 2.57 (s, 3H), 3.80 (s, 3H), 6.97 (b, 1H), 7.09 (d, 1H), 7.3–7.58 (c, 7H).

EXAMPLE 11

N-[6-Chloro-4-(2-chlorophenyl)-1,2-dihydro-1-methyl-2-oxoquinolin-3-yl]-N'-(6-methylthioquinolin-5-yl)urea 20% yield.

$^1$H NMR (300 MHz, CDCl$_3$) δ2.34 (s, 3H), 3.77 (s, 3H), 7.11 (d, 1H), 7.2–7.6 (c, 1OH), 7.77 (b, 1H), 7.98 (d, 1H), 8.78 (m, 1H).

EXAMPLE 12

N-[6-Chloro-4-(2-chlorophenyl)-1,2-dihydro-1-methyl-2-oxoquinolin-3-yl]-N'-(6-methoxyquinolin-5-yl)urea 63% yield.

$^1$H NMR (300 MHz, CDCl$_3$) δ3.77 (s, 3H), 3.79 (s, 3H), 7.0 (b, 1H), 7.11 (d, 1H), 7.2–7.63 (c, 9H), 7.70 (d, 1H), 8.00 (d, 1H), 8.74 (m, 1H).

EXAMPLE 13

N-[4,6-Bis(methylthio)-2-methylpyrimidin-5-yl]-N'-[4-(2-chlorophenyl)-1,2-dihydro-6-ethyl-1-methyl-2-oxoquinolin-3-yl]urea 19% yield.

$^1$H NMR (300 MHz, CDCl$_3$) δ1.14 (t, 3H), 2.41 (s, 6H), 2.56 (s, 3H), 2.58 (q, 2H), 3.81 (s, 3H), 6.91 (s and b, H), 7.28–7.51 (c, 6H), 7.52 (m, 1H).

EXAMPLE 14

N-[2,4-Bis(methylthio)-6-methylpyridin-3-yl]-N'-[4-(2-chlorophenyl)-1,2-dihydro-6-ethyl-1-methyl-2-oxoquinolin-3-yl]urea 19% yield.

$^1$H NMR (300 MHz, CDCl$_3$) δ1.14 (t, 3H), 2.34 (s, 3H), 2.44 (s, 3H), 2.46 (s, 3H), 2.58 (q, 2H), 3.81 (s, 3H), 6.58 (s, 1H), 6.68 (b, 1H), 6.90 (s, 1H), 7.29–7.56 (c, 7H).

EXAMPLE 15

N-4-(2-Chlorophenyl)-1,2-dihydro-6-ethyl-1-methyl-2-oxoquinolin-3-yl]-N'-(6-methylthioquinolin5-yl)urea 19% yield.

$^1$H NMR (300 MHz, CDCl$_3$) δ1.14 (t, 3H), 2.34 (s, 3H), 2.58 (q, 2H), 3.80 (s, 3H), 6.93, (s, 1H), 7.18–7.6 (c, H), 7.85 (c, 1H), 7.97 (d, 1H), 8.78 (m, 1H).

EXAMPLE 16

N-[4-(2-Chlorophenyl)-1,2-dihydro-6-ethyl-1-methyl-2-oxoquinolin-3-yl-N'-(6-methoxyquinolin-5-]urea 4% yield.

$^1$H NMR (300 MHz, CDCl$_3$) δ1.15 (t, 3H), 2.59 (q, 2H), 3.79 (s, 3H), 3.81 (s, 3H), 6.94 (s, 1H), 7.02–7.61 (c, 10H), 7.76 (d, 1h), 7.99 (d, 1H), 8.73 (m, 1H).

EXAMPLE 17

N-[2,4-Bis(methylthio)-6-methylpyridin-3-yl]-N'-[4-(2-chlorophenyl)-1,2-dihydro-6-isopropyl-1-methyl-2-oxoquinolin-3-yl]urea 32% yield.

$^1$H NMR (300 MHz, CDCl$_3$) δ 1.15 (d, 3H), 1.16 (d, 3H), 2.35 (s, 3H), 2.45 (s, 3H), 2.46 (s, 3H), 2.84 (h, 1H), 3.81 (s, 3H), 6.59 (s, 1H), 6.64 (b, 1H), 6.93 (d, 1H), 7.32–7.56 (c, 7H).

EXAMPLE 18

N-[4,6-Bis(methylthio)-2-methylpyrimidin-5-yl]-N'-[4-(2-chlorophenyl)-1,2-dihydro-6-isopropyl-1-methyl-2-oxoquinoline-3-yl]urea 29% yield.

$^1$H NMR (300 MHz, CDCl$_3$) δ1.15 (d, 3H), 1.16 (d, 3H), 2.41 (s, 6H), 2.56 (s, 3H), 2.84 (h, 1H), 3.81 (s, 3H), 6.95 (s and b, 2H), 7.34–7.58 (c, 7H).

EXAMPLE 19

N-[4-(2-chorophenyl)-1,2-dihydro-6-isopropyl-1-methyl-2-oxoquinolin-3-yl]-N'-(6-methylthioquinolin-5-yl)urea 33% yield.

$^1$H NMR (300 MHz, CDCl$_3$) δ1.15 (d, 3H), 1.16 (d, 3H), 2.32 (s, 3H), 2.84 (h, 1H), 3.79 (s, 3H), 6.98 (s, 1H), 7.2–7.62 (c, 10H), 7.81 (c, 1H), 7.95 (d, 1H), 8.77 (c, 1H).

EXAMPLE 20

N-[4-(2-Chlorophenyl)-1,2-dihydro-6-isopropyl-1-methyl-2-oxoquinolin-3-yl]-N'-(6-methoxyquinolin-5-yl)urea 10% yield.

$^1$H NMR (300 MHz, CDCl$_3$) δ1.15 (d, 3H), 1.16 (d, 3H), 2.85 (h, 1H), 3.80 (s, 3H), 3.81 (s, 3H), 6.98 (s, 1H), 7.0–7.64 (c, 10H), 7.75 (d, 1H), 8.00 (d, 1H), 8.74 (m, 1H).

EXAMPLE 21

N-[2,4-Bis(methylthio)-6-methylpyridin-3-yl]-N'-[4-(2-chlorophenyl)-1,2-dihydro-1,6-dimethyl-2-oxoquinolin-3-yl]urea 25% yield.

$^1$H NMR (300 MHz, CDCl$_3$) δ2.28 (s, 3H), 2.31 (s, 3H), 2.41 (s, 3H), 2.45 (s, 3H), 3.78 (s, 3h), 6.57 (s, 1H), 6.88 (s and b, 2H), 7.26–7.54 (c, 7H).

EXAMPLE 22

N-[4-(2-Chlorophenyl)-1,2-tithydro-1,6-dimethyl-2-oxoquinolin-3-yl]-N'-(6-methylthioquinolin-5-yl)urea 31% yield.

$^1$H NMR (300 MHz, CDCl$_3$) δ 2.27 (s, 3H), 2.29 (s, 3H), 3.77 (S, 3H), 6.93 (s, 1H), 7.17–7.62 (C, 10H), 7.78 (C, 1H), 7.92 (d, 1H), 8.74 (m, 1H).

EXAMPLE 23

N-[4,6-Bis(methylthio)-2-methylpyrimidin-5-yl]-N'-[4-(2-chlorophenyl)-1,2-dihydro-1,6-dimethyl-2-oxoquinolin-3-yl]urea 23% yield.

$^1$H NMR (300 MHz, CDCl$_3$) δ2.29 (s, 3H), 2.42 (s, 6H), 2.57 (s, 3H), 3.81 (s, 3H), 6.8 (b, 1H), 6.88 (s, 1H), 7.28–7.56 (C, 7H).

EXAMPLE 24

N-[4-(2-Chlorophenyl)-1,2-dihydro-1,6-dimethyl-2-oxoquinolin-3-yl-N'-(6-methoxyguinolin-5-yl)urea 13% yield.

$^1$H NMR (300 MHz, CDCl$_3$) δ2.30 (s, 3H), 3.79 (s, 3H), 3.80 (s, 3H), 6.92 (s, 1H), 6.94–7.63 (c, 1OH), 7.77 (d, H), 7.99 (d, 1H), 8.73 (m, 1H).

EXAMPLE 25

N-[6-Chloro-4-(2-chlorophenyl)-1,2-dihydro-1-methyl-2-oxoquinolin-3-yl]-N'-(6-dimethylaminoquinolin-5-yl)urea 72% yield.

$^1$H NMR (300 MHz, DMSO-d$_6$) δ2.63 (s, 6H), 3.79 (s, 3H), 6.87 (d, 1H), 7.25–7.7 (c, 9H), 7.78 (d, 1H), 8.2 (s, 1H), 8.46 (b, 1H), 8.66 (q, 1H).

EXAMPLE 26

N-[6-Chloro-4-(2-chlorophenyl)-1,2-dihydro-1-methyl-2-oxoquinolin-3-yl]-N'-(2-dimethylamino-6-methyl-4-methylthiopyridin-3-yl)urea 22% yield.

$^1$H NMR (300 MHz, CDCl$_3$) δ2.33 (s, 3H), 2.39 (s, 9H), 3.78 (s, 3H), 6.45 (s, 1H), 7.03 (d, 1H), 7.26–7.52 (c, 8H), 7.33 (2d, 2H), 7.44–7.64 (c, 7H).

EXAMPLE 27

N-[6-Chloro-4-(2-chlorophenyl)-1,2-dihydro-1-methyl-2-oxoquinolin-3-yl]-N'-(6-methoxyisoquinolin-5-yl)urea 10% yield.

$^1$H NMR (300 MHz, CDCl$_3$) d 3.79 (s, 3H), 3.84 (s, 3H), 7.1 (b, 1H), 7.13 (d, 1H), 7.33 (2d, 2H), 7.44–7.64 (c, 7H), 7.87 (d, 1H), 8.31 (b, 1H), 9.1 (b, 1H).

I claim:

1. A compound of the formula

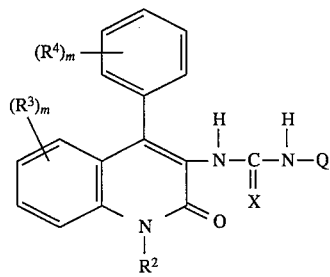

(I)

wherein each m is independently selected from 0 to 4;

$R^2$ is selected from hydrogen and (C$_1$-C$_6$) alkyl;

Each $R^3$ and $R^4$ is independently selected from halogen, (C$_1$-C$_6$) alkyl optionally substituted with one or more halogen atoms, (C$_1$-C$_6$) alkoxy optionally substituted with one or more halogen atoms, (C$_1$-C$_6$) alkylthio optionally substituted with one or more halogen atoms; nitro, carboxyl optionally esterified with a (C$_1$-C$_6$) alkyl group; hydroxyl, (C$_1$-C$_4$) acyloxy and (C$_1$-C$_3$) acyl;

X is sulfur or oxygen; and

Q is a group of the formula

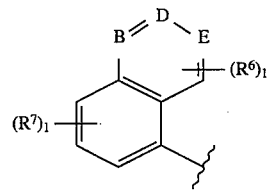

XIV

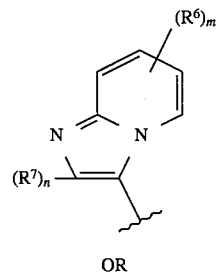

XV

OR

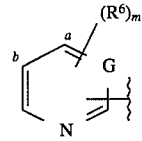

XVI wherein m is as defined above;

n is 0 or 1.

Each 1 is independently selected from 0 to 3;

Each $R^6$ and $R^7$ is independently selected from the group consisting of halogen, (C$_1$-C$_6$)alkyl, (C$_1$-C$_6$) haloalkyl, optionally halogenated (C$_1$-C$_6$)alkoxy, (C$_1$-C$_6$) alkylthio, (C$_5$-C$_7$) cycloalkylthio, optionally substituted phenyl-(C$_1$-C$_6$) alkylthio, substituted phenylthio, heteroarylthio, heteroaryloxy, (C$_1$-C$_6$) alkylsulfinyl, (C$_1$-C$_6$) alkylsulfonyl, (C$_5$-C$_7$) cycloalkylsulfinyl, (C$_5$-C$_7$) cycloalkylsulfonyl, phenyl (C$_1$-C$_6$) alkylsulfinyl, phenyl (C$_1$-C$_6$) alkylsulfonyl, substituted phenylsulfinyl, substituted phenylsulfonyl, heteroarylsulfinyl, heteroarylsulfonyl, and NR$^{10}$R$^{11}$, wherein R$^{10}$ and R$^{11}$ are the same or different and are selected from the group consisting of hydrogen, (C$_1$-C$_6$) alkyl, optionally substituted phenyl, (C$_1$-C$_6$) acyl and optionally substituted aroyl, wherein said substituted phenyl and substituted aroyl groups are substituted with one or more substituents independently selected from the group consisting of $(C_1-C_6)$ alkyl, $(C_1-C_6)$ alkoxy, $(C_1-C_6)$ alkylthio, halogen and trifluoromethyl, or $R^{10}$ and $R^1$ together with the nitrogen to which they are attached, form a piperidine, pyrrolidine or morpholine ring;

B, D, E and G are selected from the group consisting of nitrogen and carbon, with the proviso that one or more of B, D and E is nitrogen, and with the proviso that when G is nitrogen, the group XVI is attached to the nitrogen of formula I at the 4 or 5 position of the pyrimidine ring (designated by a and b) wherein any of said nitrogens may be oxidized, or a pharmaceutically acceptable salt of such a compound.

2. A compound according to claim 1, wherein Q is 6-$(C_1-C_3)$alkoxyquinolin-5-yl, 6-$(C_1-C_3)$alkylthioquinolin-5-yl, 6-$(C_1-C_3)$alkylquinolin-5-yl, 6-$(C_1-C_3)$ alkylthioisoquinolin-5-yl, 6-$(C_1-C_3)$alkoxyisoquinolin-5-yl, 4,6-bis[$(C_1-C_3)$alkylthio]-2-methylpyrimidin-5-yl, 4,6-bis[$(C_1-C_3)$alkylthio]pyrimidin-5-yl, 2,4-bis[$(C_1-C_3)$alkylthio]-6-methylpyridin-3-yl or 2,4-bis[$(C_1-C_3)$alkylthio]pyridin-3-yl.

3. A compound according to claim 2, wherein $R^2$ is methyl, m is at least one and $R^3$ and $R^4$ are defined as above with the proviso that at least one of $R^3$ is 6-halo or 6-alkyl and at least one of $R^4$ is 2-halo.

4. A compound according to claim 1, wherein said compound is selected from the group consisting of N-[2,4-Bis(methylthio)-6-methylpyridin-3-yl]-N'-[6-chloro- 4-(2-chlorophenyl)-1,2-dihydro-1-methyl-2-oxoquinolin-3-yl]urea;

N-[4,6-Bis(methylthio)2-methylpyrimidin-5-yl]-N'-[6-chloro- 4-(2-chlorophenyl)-1,2-dihydro-1-methyl-2-oxoquinolin-3-yl]urea;

N-[6-Chloro-4-(2-chlorophenyl)-1,2-dihydro-1-methyl-2-oxoquinolin- 3-yl]-N'-(6-methylthioquinolin-5-yl)urea; and N-[6-Chloro-4-(2-chlorophenyl)-1,2-dihydro-1-methyl-2-oxoquinolin- 3-yl]-N'-(6-methoxyquinolin-5-yl)urea;

N-[4,6-Bis(methylthio)-2-methylpyrimidin-5-yl]-N'-[4-(2-chlorophenyl)-1,2-dihydro-6-ethyl-1-methyl-2-oxoquinolin-3-yl]urea;

N-[2,4-Bis(methylthio)-6-methylpyridin-3-yl]-N'-[4-(2-chlorophenyl)- 1,2-dihydro-6-ethyl-1-methyl-2-oxoquinolin-3-yl] urea;

N-4-(2-Chlorophenyl)-1,2-dihydro-6-ethyl-1-methyl-2-oxoquinolin- 3-yl]-N'-(6-methylthioquinolin-5-yl)urea;

N-[4-(2-Chlorophenyl)-1,2-dihydro-6-ethyl-1-methyl-2-oxoquinolin- 3-yl]-N'-(6-methoxyquinolin-5-yl]urea;

N-[2,4-Bis(methylthio)-6-methylpyridin-3-yl]-N'-[4-(2-chlorophenyl)- 1,2-dihydro-6-isopropyl-1-methyl-2oxoquinolin-3-yl]urea;

N-[4,6-Bis(methylthio)-2-methylpyrimidin-5-yl]-N'-[4-(2-chlorophenyl)-1,2-dihydro-6-isopropyl-1-methyl-2-oxoquinolin-3-yl]urea;

N-[4-(2-Chlorophenyl)-1,2-dihydro-6-isopropyl-1-methyl- 2-oxoquinolin-3-yl]-N'-(6-methylthioquinolin-5-yl)urea;

N-[4-(2-Chlorophenyl)-1,2-dihydro-6-isopropyl-1-methyl- 2-oxoquinolin-3-yl]-N'-(6-methoxyquinolin-5-yl)urea;

N-[2,4-Bis(methylthio)-6-methylpyridin-3-yl]-N'-[4-(2-chlorophenyl)- 1,2-dihydro-1,6-dimethyl-2-oxoquinolin-3-yl] urea;

N-[4-(2-Chlorophenyl)-1,2-dihydro-1,6-dimethyl-2-oxoquinolin- 3-yl]-N'-(6-methylthioquinolin-5-yl)urea;

N-[4,6-Bis(methylthio)-2-methylpyrimidin-5-yl]-N'-[4-(2-chlorophenyl)-1,2-dihydro-1,6-dimethyl-2-oxoquinolin-3-yl]urea;

N-[4-(2-Chlorophenyl)-1,2-dihydro-1,6-dimethyl-2-oxoquinolin- 3-yl]-N'-(6-methoxyquinolin-5-yl)urea;

N-[6-Chloro-4-(2-chlorophenyl)-1,2-dihydro-1-methyl-2-oxoquinolin- 3-yl]-N'-(6-dimethylaminoquinolin-5-yl)urea;

N-[6-Chloro-4-(2-chlorophenyl)-1,2-dihydro-1-methyl-2-oxoquinolin- 3-yl]-N'-(2-dimethylamino-6-methyl-4-methylthiopyridin-3-yl)urea;

N-[6-Chloro-4-(2-chlorophenyl)-1,2-dihydro-1-methyl-2-oxoquinolin- 3-yl]-N'-(6-methoxyisoquinolin-5-yl)urea.

5. A compound according to claim 1 wherein Q is selected from the group consisting of 6-methoxyquinolin-5-yl, 6-methylthioquinolin-5-yl, 6-methoxyisoquinolin-5-yl, 6-methylthioisoquinolin-5-yl, 2-methyl- 4,6-(bismethylthio)pyrimidin-5-yl, 6-methyl-2,4 -bis(methylthio)pyridin-3-yl, 2,4-bis(ethylthio)pyridin-3-yl, 2,4-dimethoxy-6-methylpyridin-3-yl, 2,4,6-trimethylpyridin- 3-yl, 6-(4-methoxyphenylthio)quinolin-5-yl and 6-pentylthioquinolin-5-yl.

6. A compound according to claim 1 wherein at least one hydrogen or carbon atom thereof comprises a radioactive isotope.

7. A compound according to claim 6, wherein said radioisotope is tritium or carbon-14.

8. The compound of claim 7 wherein the hydrogen radioisotope is tritium.

9. The compound of claim 7 wherein the carbon radioisotope is carbon-14.

10. A pharmaceutical composition for inhibiting acyl coenzyme A: cholesterol acyltransferase, inhibiting intestinal absorption of cholesterol, reversing or slowing the development of atherosclerosis, or lowering the concentration of serum cholesterol in a mammal, comprising an amount of a compound according to claim 1 that is effective in inhibiting acyl coenzyme A: cholesterol acyltransferase or intestinal absorption of cholesterol, or is effective in reversing or slowing the development of atherosclerosis or lowering the concentration of serum cholesterol, and a pharmaceutically acceptable carrier.

11. A method for inhibiting acyl coenzyme A: cholesterol acyltransferase, inhibiting intestinal absorption of cholesterol, reversing or slowing the development of atherosclerosis, or lowering the concentration of serum cholesterol in a mammal, comprising an amount of a compound according to claim 1 that is effective in inhibiting acyl coenzyme A: cholesterol acyltransferase or intestinal absorption of cholesterol, or is effective in reversing or slowing the development of atherosclerosis or lowering the concentration of serum cholesterol and a pharmaceutically acceptable carrier.

* * * * *